(12) United States Patent
Johnson et al.

(10) Patent No.: US 7,050,160 B1
(45) Date of Patent: May 23, 2006

(54) PROCESS AND APPARATUS FOR INTEGRATING SHEET RESISTANCE MEASUREMENTS AND REFLECTANCE MEASUREMENTS OF A THIN FILM IN A COMMON APPARATUS

(75) Inventors: Walter H. Johnson, San Jose, CA (US); Jagadish Kalyanam, San Jose, CA (US); Shankar Krishnan, Santa Clara, CA (US); Murali K. Narasimhan, San Jose, CA (US)

(73) Assignee: KLA-Tencor Technologies Corporation, Milpitas, CA (US)

( * ) Notice: Subject to any disclaimer, the term of this patent is extended or adjusted under 35 U.S.C. 154(b) by 277 days.

(21) Appl. No.: 10/407,669

(22) Filed: Apr. 3, 2003

Related U.S. Application Data

(60) Provisional application No. 60/417,990, filed on Oct. 11, 2002.

(51) Int. Cl.
*G01N 21/00* (2006.01)

(52) U.S. Cl. .......................................... 356/73; 356/630

(58) Field of Classification Search ................. 356/73, 356/630, 445, 448; 324/752, 765; 250/492.21, 250/492.2, 492.1, 441.11, 309
See application file for complete search history.

(56) References Cited

U.S. PATENT DOCUMENTS

| | | | |
|---|---|---|---|
| 3,609,537 A | * | 9/1971 | Healy et al. ................. 324/601 |
| 3,676,775 A | * | 7/1972 | Dupnock et al. ............ 324/717 |
| 5,552,704 A | | 9/1996 | Mallory et al. .............. 324/233 |
| 6,393,915 B1 | * | 5/2002 | Banet et al. ................... 73/579 |
| 6,417,515 B1 | * | 7/2002 | Barrett et al. ........... 250/492.21 |
| 6,608,495 B1 | * | 8/2003 | Sarfaty et al. .............. 324/752 |
| 6,707,540 B1 | * | 3/2004 | Lehman et al. ............... 356/72 |

* cited by examiner

*Primary Examiner*—Gregory J. Toatly, Jr.
*Assistant Examiner*—Ray M. Punnoose
(74) *Attorney, Agent, or Firm*—John P. Taylor

(57) ABSTRACT

A process for measuring both the reflectance and sheet resistance of a thin film, such as a metal film or a doped semiconductor, in a common apparatus comprises: directing a beam of radiation from a radiation source on the common apparatus onto a portion of the surface of the thin film, sensing the amount of radiation reflected from the surface of the thin film, and contacting the surface of the thin film with a sheet resistance measurement apparatus on the apparatus at a portion of the surface of the thin film coincident with or adjacent to the portion of the thin film contacted by the radiation beam to measure the sheet resistance of the thin film. The sheet resistance measurement apparatus may, by way of example, comprise a 4 point probe or an eddy current measurement apparatus. The respective measurements may be carried out either simultaneously or sequentially. By deriving the resistivity of the thin film from the measured reflectance at any particular region of the thin film surface, the thickness of the thin film, at that region of the film, may be obtained by dividing the derived resistivity by the measured sheet resistance for that same region.

24 Claims, 5 Drawing Sheets

MEASURING BOTH THE REFLECTANCE AND THE SHEET RESISTANCE OF A THIN FILM IN THE SAME CHAMBER COMPRISES MOUNTING IN A CHAMBER A SHEET RESISTANCE MEASUREMENT APPARATUS SUCH AS 4 POINT PROBE APPARATUS OR AN EDDY CURRENT MEASUREMENT APPARATUS CAPABLE OF MEASURING SHEET RESISTANCE OF A THIN FILM;

MOUNTING, IN THE SAME CHAMBER AND ADJACENT THE SHEET RESISTANCE MEASUREMENT APPARATUS, AN APPARATUS CAPABLE OF MEASURING REFLECTANCE OF A THIN FILM;

MOUNTING A THIN FILM IN THE SAME CHAMBER;

DIRECTING A BEAM OF RADIATION FROM THE REFLECTANCE MEASUREMENT APPARATUS ONTO A PORTION OF THE THIN FILM SURFACE;

SENSING THE RADIATION REFLECTED BACK FROM THE THIN FILM SURFACE TO MEASURE THE REFLECTIVITY OF THE THIN FILM SURFACE; AND

OPERATIONALLY CONTACTING, WITH THE SHEET RESISTANCE MEASUREMENT APPARATUS, THE THIN FILM SURFACE ADJACENT TO THE THIN FILM SURFACE CONTACTED BY THE RADIATION BEAM, TO MEASURE THE THIN FILM SHEET RESISTANCE.

FIG. 9

PROCESS AND APPARATUS FOR INTEGRATING SHEET RESISTANCE MEASUREMENTS AND REFLECTANCE MEASUREMENTS OF A THIN FILM IN A COMMON APPARATUS

This application claims the benefit of U.S. Provisional Application Ser. No. 60/417,990, filed Oct. 11, 2002.

BACKGROUND OF THE INVENTION

1. Field of the Invention

This invention relates to a process for measuring the sheet resistance of a thin film such as a metal film or an ion implanted layer, and the reflectance of the thin film in the same apparatus either simultaneously or sequentially.

2. Description of the Related Art

Apparatus, such as a 4 point probe or an eddy current tool, is commercially available for measuring the sheet resistance of a thin film such as, for example, a metal film, For example, a 4 point probe apparatus to measure the sheet resistance of a thin film is available from KLA-Tencor as an Omnimap© RS-100™ tool. An example of an eddy current tool to measure the sheet resistance of a thin film is the Omnimap© NC110™ tool previously available from KLA-Tencor. Apparatus is also available commercially for the measurement of the reflectance of a thin film such as a metal film or an ion implanted layer, An example of such an apparatus is KLA-Tencor's ASET-F5 Tool.

While the use of separate measurement tools, to respectively determine the sheet resistance and the reflectance of a particular thin film, has been satisfactory in the past, the costs of individual tools and separate vacuum chambers to carry out the individual processes, as well as the fab footprint requirements, including the added process time, make it less and less attractive to carry out individual measurements of the sheet resistance and the reflectance of a thin film such as a metal film in separate apparatus.

In addition, carrying out the respective measurements in separate apparatus means that measurement spots on the thin film for reflectance measurements may not correlate with prior locations used for sheet resistance measurements made by either a 4 point probe or an eddy current to measure the sheet resistance of a thin film,

SUMMARY OF THE INVENTION

The invention comprises a process and an apparatus for measuring both the reflectance and sheet resistance of a thin film such as a metal film in a common apparatus comprises: directing a beam of radiation from a radiation source onto a portion of the surface of the thin film, sensing the amount of radiation reflected from the surface of the thin film, and measuring the sheet resistance of the thin film on or adjacent to the portion of the thin film contacted by the radiation beam either by contacting the surface of the thin film with a 4 point probe or by an eddy current method such as described in U.S. Pat. No. 5,552,704. The respective measurements may be carried out either simultaneously or sequentially. By deriving the resistivity of the thin film from the measured reflectance, the thickness of the thin film, at any particular region of the film, may be obtained by dividing the derived resistivity by the measured sheet resistance for that region.

BRIEF DESCRIPTION OF THE DRAWINGS

FIG. 9 is a flow sheet illustrating the process of the invention.

DETAILED DESCRIPTION OF THE INVENTION

Figure 1:
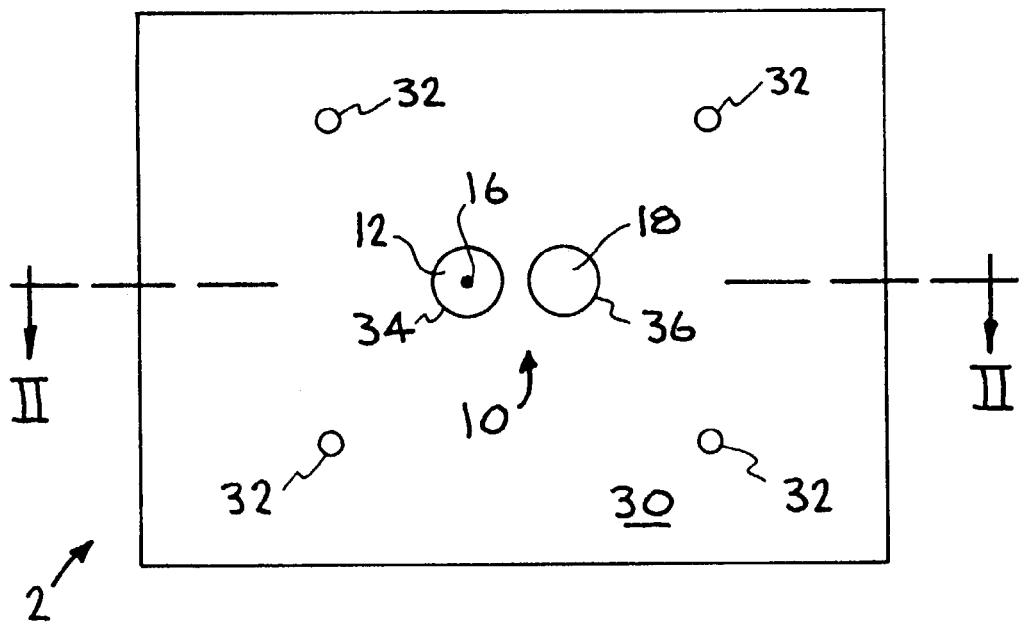
FIG. 1 is a top view of one embodiment of the invention wherein a 4 point probe is used for measuring the sheet resistance, and an apparatus for measuring the reflectance of the thin film surface are mounted in coincidence with one another.

In accordance with the invention, a process and apparatus is disclosed for measuring both the reflectance and sheet resistance of a thin film such as a metal film in a common apparatus. The process comprises: measuring the reflectance of a thin film by directing a beam of radiation from a radiation source onto a portion of the surface of the thin film, and sensing the amount of radiation from the radiation beam reflected from the surface of the thin film; and determining the sheet resistance of the thin film either by contacting the surface of thin film with a 4 point probe adjacent or coincident to the portion of the thin film contacted by the radiation beam, or by means of an eddy current probe. The respective measurements may be carried out either simultaneously or sequentially.

The measured reflectance of the thin film can be correlated to resistivity (which is a bulk material property). In the case of metal thin films, the grain structure of a metal film will effect both the reflectance and the resistivity (and therefore the sheet resistance). In the case of ion implantation, prior to annealing out the damage, the increase in ion dose will increase the damage and therefore increase the scattering, After annealing, the dose effects the resistivity. This relationship between the measured reflectance and the resistivity can, for any given thin film, be empirically determined. Table I shows the measured reflectance intensity of a thin doped silicon film after the thin silicon film has been exposed to various doses, respectively, of boron, phosphorus, or arsenic which, in turn, affect the resistivity of the thin film, thus showing the correlation between the reflectance of a doped semiconductor film and the respective resistivities of the various silicon film to varying dosages of boron, phosphorus, and arsenic.

TABLE I

| | RELATIVE REFLECTIVE INTENSITY | | |
|---|---|---|---|
| DOSAGE | BORON | PHOSPHORUS | ARSENIC |
| 1E + 11 | 200 | 400 | 500 |
| 2E + 11 | 225 | 500 | 650 |
| 3E + 11 | 250 | 600 | 735 |
| 4E + 11 | 275 | 650 | 810 |
| 5E + 11 | 300 | 660 | 830 |
| 6E + 11 | 325 | 670 | 840 |
| 7E + 11 | 350 | 680 | 860 |
| 8E + 11 | 375 | 690 | 870 |
| 9E + 11 | 400 | 700 | 880 |
| 1E + 12 | 420 | 705 | 900 |
| 1.5E + 12 | 500 | 720 | 920 |
| 2E + 12 | 570 | 750 | 975 |
| 3E + 12 | 650 | 825 | 1100 |
| 4E + 12 | 700 | 850 | 1150 |
| 5E + 12 | 750 | 875 | 1200 |
| 6E + 12 | 775 | 900 | 1200 |
| 7E + 12 | 800 | 925 | 1300 |
| 8E + 12 | 825 | 950 | 1400 |
| 9E + 12 | 850 | 975 | 1500 |
| 1E + 13 | 875 | 1000 | 1600 |
| 2E + 13 | 1000 | 1300 | 2200 |
| 3E + 13 | 1200 | 1600 | 3000 |
| 4E + 13 | 1400 | 1900 | 3850 |
| 5E + 13 | 1500 | 2200 | 4900 |
| 6E + 13 | 1600 | 2500 | 6500 |
| 7E + 13 | 1800 | 2800 | 8000 |
| 8E + 13 | 1900 | 3300 | 10000 |
| 9E + 13 | 2000 | 3600 | 12000 |
| 1E + 14 | 2100 | 3800 | 14000 |
| 2E + 14 | 2200 | 4000 | 17000 |

Table II shows the relationship of the thickness of a metal film of aluminum on a silicon substrate to reflectance intensity of the aluminum film for various wavelengths of light, thereby permitting derivation of the thickness of the metal film directly from the measured reflectance of the aluminum metal film. It should be noted here that the data shown in Table II is only representative of the look up table which may be used to determine the thickness of an aluminum film by the measured reflection at a given wavelength of radiation. It will also be noted from the data presented in table II that the reflectance changes at any particular thickness of the aluminum film are greater at low frequencies than at higher frequencies, indicating that the use of a lower frequency radiation source may result in a more accurate determination of the thickness of the aluminum film.

TABLE II (RELATIVE REFLECTION INTENSITIES AT VARIOUS WAVELENGTHS FOR VARIOUS THICKNESSES OF ALUMINUM FILM ON SILICON)

| WAVE-LENGTH OF LIGHT | THICKNESS OF ALUMINUM FILM (ANGSTROMS) | | | | |
|---|---|---|---|---|---|
| (NM) | 0 | 50 | 100 | 200 | 400 |
| 239.829 | 0.00813905 | 0.312563 | 0.702759 | 0.859355 | 0.926923 |
| 307.884 | 0.0646642 | 0.475432 | 0.781992 | 0.887965 | 0.924209 |
| 377.52 | 0.157407 | 0.593874 | 0.82765 | 0.898968 | 0.924657 |
| 446.199 | 0.260451 | 0.672798 | 0.853452 | 0.906456 | 0.924083 |
| 513.921 | 0.355207 | 0.726638 | 0.869369 | 0.909701 | 0.92339 |
| 580.686 | 0.434696 | 0.761829 | 0.876619 | 0.907466 | 0.918823 |
| 646.494 | 0.499424 | 0.784416 | 0.878891 | 0.903657 | 0.911676 |
| 711.345 | 0.548006 | 0.795869 | 0.874911 | 0.895111 | 0.901427 |
| 775.239 | 0.579116 | 0.790665 | 0.855141 | 0.870481 | 0.882623 |

Thus, the reflectance of the film may be used to determine directly the thickness of the metal film, while in the case of a doped silicon film, the reflectance may be used, with look up tables, to determine the resistivity of the thin film and from this derived resistivity divided by the measured sheet resistance, one may calculate the thickness of the thin film for the region where the sheet resistance and the reflection were both respectively measured.

The term "thin film", as used herein, is intended to define a film of metal, a doped semiconductor film, or an insulating film such as an oxide film or photoresist film, having a thickness not exceeding about 500 micrometers (μm), and preferably not exceeding about 100 μm.

Figure 2:
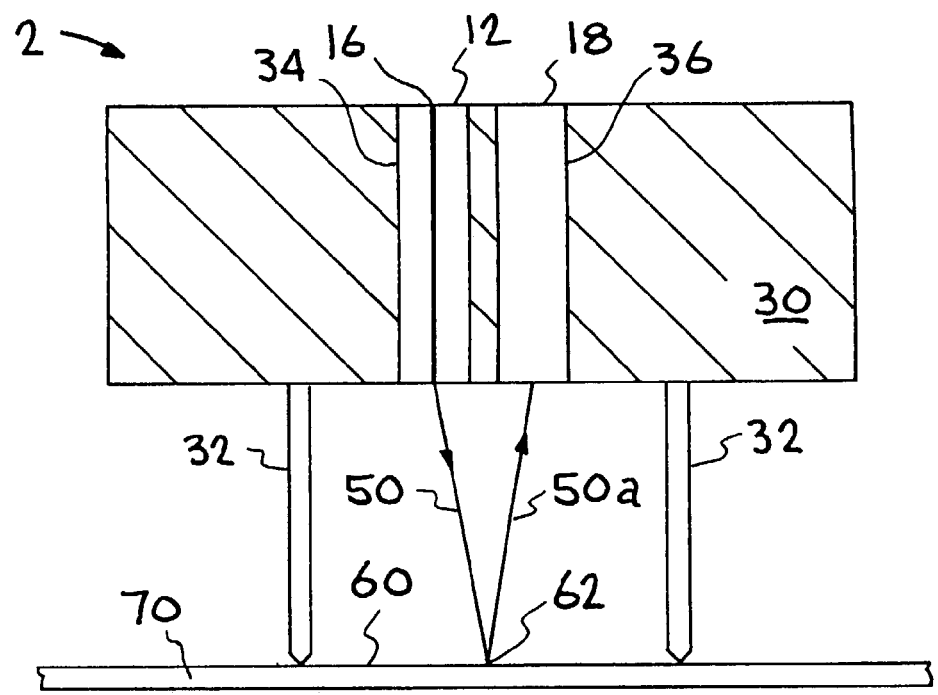
FIG. 2 is a vertical cross-sectional view of the apparatus of FIG. 1 taken alone lines II—II.

Turning now to FIGS. 1 and 2, apparatus, generally indicated at arrow 2, is shown for carrying out the preferred embodiment of the process of the invention. In this embodiment of the invention, reflectance apparatus 10 for measuring the reflectance of a thin film is illustrated as generally centrally mounted on a sheet resistance measurement probe apparatus, such as illustrated 4 point probe apparatus 30, for measuring the sheet resistance of a thin film such as the thin film shown at 60 in FIG. 2.

It should be noted that while the use of a 4 point probe as the sheet resistance measurement apparatus is described and illustrated herein, this is by way of illustration and not of limitation. It will be understood, that when the use of a 4 point sheet resistance measurement probe is described and illustrated, other sheet resistance measurement apparatus, such as an eddy current probe, may be substituted for the 4 point probe.

As best seen in the view of FIG. 1, reflectance apparatus 10 may be generally mounted on a sheet resistance measurement apparatus such as a point probe apparatus 30 so that the 4 pins 32, for example, of 4 point probe apparatus 30 are coaxially disposed around reflectance apparatus 10 to provide for coincident operation of the reflectance apparatus and the sheet resistance measurement probe apparatus during either simultaneous or sequential operation of the respective apparatuses during the process.

Reflectance apparatus 10, as seen in both FIGS. 1 and 2, comprises a radiation source shown at 12, and a sensor shown at 18 mounted, preferably, side by side and, generally in the center of 4 point probe apparatus 30 (as best seen in FIG. 1). Radiation source 12 may comprise a fiber optic cable 16 mounted in a first bore 34 in 4 point probe apparatus 30, with the end of fiber optic cable 16 providing a beam of radiation 50 directed toward a particular portion 62 of the surface of thin film 60 shown, in FIG. 2, mounted on a substrate 70. While bore 34 is shown almost perpendicular to the base of 4 point probe apparatus 30, it will be recognized by those skilled in the art that fiber optic cable 16 in bore 34 must be tilted to provide a radiation 50 beam which, when reflected back to reflectance apparatus 30 from thin film 60 as reflected beam 50a, will be intercepted by sensor 18. In another embodiment, radiation would be directed through bore 34 in 4 point probe apparatus 30 by means of optical lenses (not shown) focused to a known spot size. This latter radiation beam would, of course, also need to be slightly angled to permit reflection of the beam back to sensor 18.

In either embodiment, the radiation source for radiation beam 50 may comprise a single wavelength source such as an LED or a multiple wavelength source such as a Xenon arc lamp with filters used to select the desired wavelength. e.g., about 433 nm.

Sensor 18 is shown generally centrally mounted on 4 point probe apparatus 30, within or above a second bore 36 on 4 point probe apparatus 30 which provide ingress and egress for the electrical connections to sensor 18. As previously discussed with respect to a tilt of bore 34 with fiber optics cable 16 therein, sensor 18 also must be mounted slightly tilted to intercept the reflected radiation beam 50a being reflected back from the surface of thin film 60 on substrate 70. Sensor 18 may comprise any commercially available sensor sensitive to the wavelength of reflected radiation beam 50a. An example of such a commercially available sensor is a Zeiss MMS1.

The sheet resistance measurement probe apparatus may comprise any commercially available point probe apparatus such as previously mentioned Omnimap® RS-100™ tool, available from KLA-Tencor, the assignee of this invention. Other sources of 4 point probe apparatus include Kokusai Electric and Creative Design Engineering (CDE). When the sheet resistance measurement probe apparatus comprises an eddy current probe, it may comprise any commercially available eddy current probe apparatus such as, for example, an OmniMap NC110, a Tencor M-Gage, an ADE 7200, or a Lehighton Electronics LEI 1510.

While any sheet resistance measurement probe, such as, for example, a 4 point probe mechanism or an eddy current measurement apparatus, could be used in the practice of the process of the invention, it should be noted that, preferably, the sheet resistance measurement apparatus used will be an apparatus which permits the reflectance apparatus to be either generally concentrically mounted on the sheet resistance measurement apparatus, e.g., on 4 point probe apparatus 30 or at least mounted on the side of the sheet resistance measurement apparatus, such as the illustrated 4 point probe apparatus.

This permits either the same portion of the surface of the thin film to be measured for sheet resistance and reflectivity or at least permits the respective reflectance and sheet resistance measurements of closely spaced apart adjacent portions of the surface. This is particularly important, for example, when the two measurements (reflectance and sheet resistance) are used to determine thickness of the thin film, as will be discussed below. By "closely spaced apart" regions of the thin film for the respective measurement of the sheet resistance and the reflectivity is meant a distance on the thin film surface not exceeding 10 millimeters (mm), and preferably not exceeding 1 mm.

As integrated circuit structures which utilize the thin films measured by the process of this invention become smaller and smaller, and as the use of a mechanical abrasion planarization process such as chemical mechanical polishing (CMP) becomes more prevalent, accurate determination of the thickness of the thin film becomes of great importance. The process of the invention, by carrying out both reflectance and sheet resistance measurements on the same portion of the surface of the thin film—or at least on closely spaced apart regions of the thin film surface—can be used to provide a more accurate determination of the thickness of the thin film at a particular portion of the film surface.

The thickness of a thin film can be calculated by dividing the resistivity of the thin film by the sheet resistance of the thin film (the measurement made by the 4 point probe apparatus). The resistivity of a thin film is related to the variations in reflectivity of the thin film under some conditions (one of the parameters measured by the process of the invention). For example, for thin films, the surface roughness of the thin film will have an effect on both the reflectance and the resistivity of the thin film. The resistivity of the thin film may be derived from the measured reflectance of the thin film as follows: The reflectance of a series of samples numbering about five is measured and correlated to the resistivity values determined from the sheet resistance values and the thin film thickness as measured by the step profile. The step profile is determined by etching a small area of the surface of the thin film and dragging a stylus across the step as is common with systems such as the KLA-Tencor HRP.

It should be noted that the respective reflectance and sheet resistance measurements may be carried out by the process of the invention either simultaneously or sequentially, and on the same or closely spaced apart regions of the surface of the thin film, except that when the measurement are carried out sequentially on the same region of the surface of the thin film, it is preferable to carry out the reflectance measurement first because of possible damage to the thin film surface by the pins of the 4 point probe apparatus. It should be noted that the respective reflectance and sheet resistance measurements may be carried out by the process of the invention either simultaneously or sequentially, and on the same or closely spaced apart regions of the surface of the thin film, except that when the measurement are carried out sequentially on the same region of the surface of the thin film, it is preferable to carry out the reflectance measurement first because of possible damage to the thin film surface by the pins of the 4 point probe apparatus.

Figure 3:
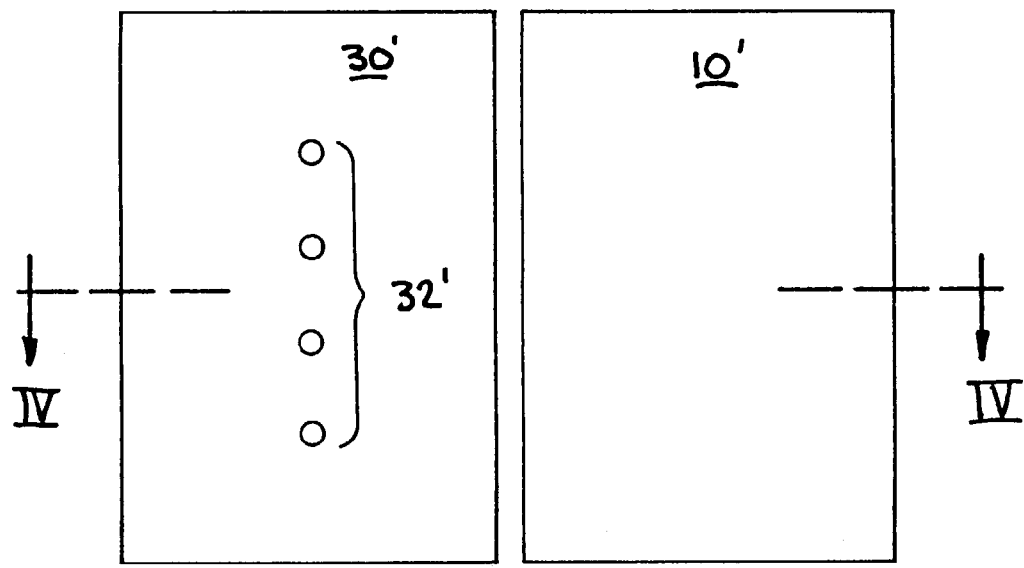
FIG. 3 is a top view of another embodiment of the invention wherein a 4 point probe is used for measuring the sheet resistance, and the apparatus for measuring the reflectance of the thin film surface, are mounted adjacent one another.
Figure 4:
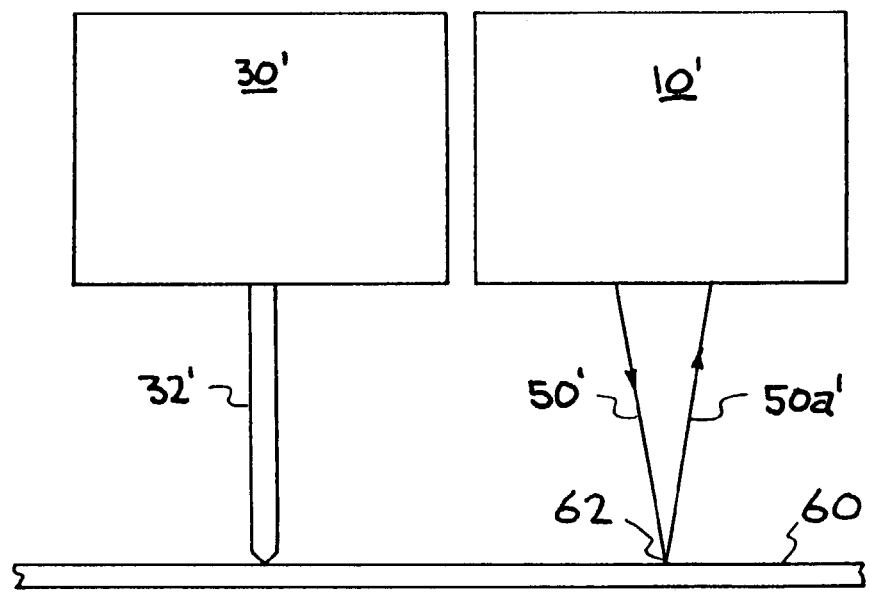
FIG. 4 is a vertical cross-sectional view of the apparatus of FIG. 3 taken alone lines IV—IV.

Turning now to FIGS. 3 and 4, another embodiment of the process of the invention is shown wherein the respective measurements of the reflectance and the sheet resistance of the thin film are carried out with reflectance apparatus 10' and 4 point probe apparatus 30' mounted side by side rather than coincident. In the illustrated embodiment pins 32' on 4 point probe apparatus 30' are shown mounted in a line rather than in the cubic arrangement shown inn FIG. 1 of the previous embodiment. As in the previous embodiment, the same radiation source (not shown) and the same sensor (also not shown) may be used and each must be slightly tilted to insure that radiation beam 50' is reflected off thin film 60 as reflected beam 50a back to the sensor.

This embodiment is of greatest interest where it is not desired or needed to make the reflectance and sheet resistance measurements on the same region or portion of the thin film, but rather the respective reflectance and sheet resistance values of closely spaced apart regions will suffice. Since two closely spaced apart regions are measured, rather than the same region, there are no complications from conducting the process in a simultaneous mode rather than a sequential mode.

Figure 5:
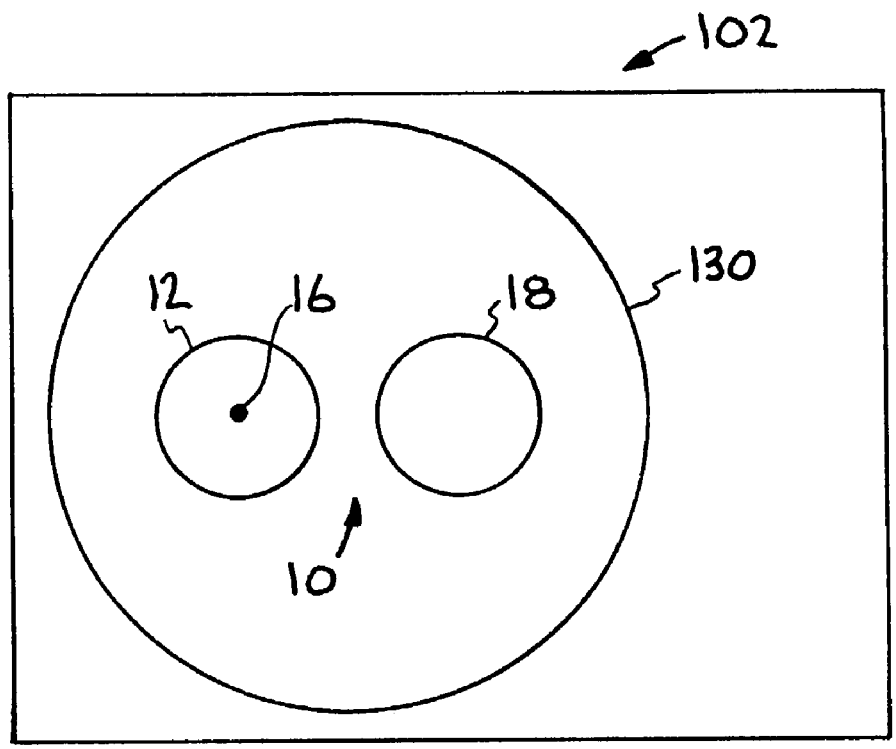
FIG. 5 is a top view of another embodiment of the invention wherein the apparatus used for measuring the reflectance of thin film is mounted in an apparatus coincident with an eddy current coil tool used for measuring the sheet resistance of the thin film.
Figure 6:
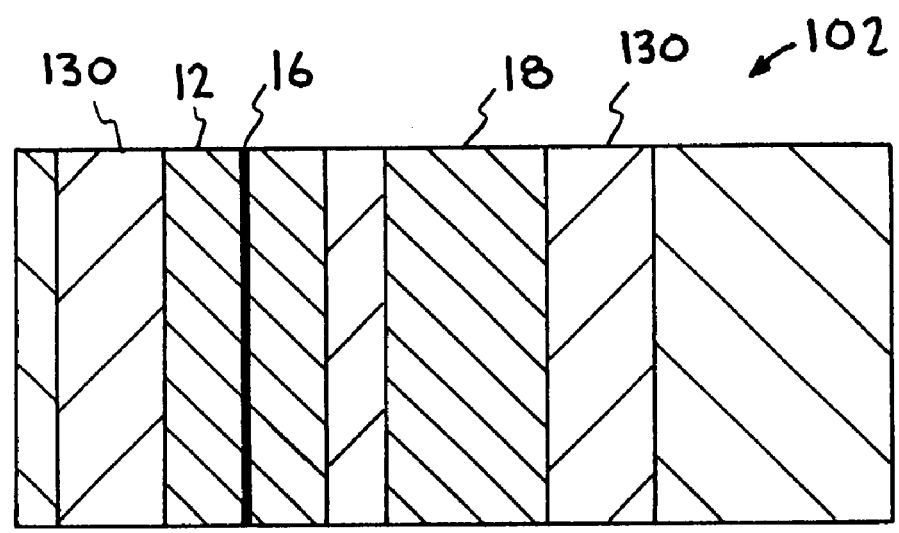
FIG. 6 is a vertical cross-section view of the apparatus of FIG. 5.

FIGS. 5 and 6 illustrate another embodiment of the invention wherein the reflectance nd the sheet resistance of a thin film, such as thin film 60, are, in accordance with the invention, measured by the same apparatus either simultaneously or sequentially. In this embodiment, the reflectance may be measured using the same reflectance measurement apparatus 10 previously described with respect to FIGS. 1–4. However, the sheet resistance is measured using an eddy current sheet resistance measurement tool 130 such as described in previously referred to U.S. Pat. No. 5,552,704, assigned to he assignee of this invention, the subject matter of which is hereby incorporated by reference, and cross-reference to which is hereby made.

Reflectance measurement apparatus 10 and eddy current sheet resistance measurement apparatus 130 may be operated either simultaneously or sequentially, as in the embodiments of FIGS. 1–4. However, in either of the two cases, the same area or regions of the thin film is preferably measured by both the reflectance measurement tool and the eddy current sheet resistance measurement apparatus to maximize the information or data collected on a given and definable space or region of the thin film. Furthermore, as previously discussed, this permits determination of the thickness of the thin film at that point or region of the thin film.

Figure 7:
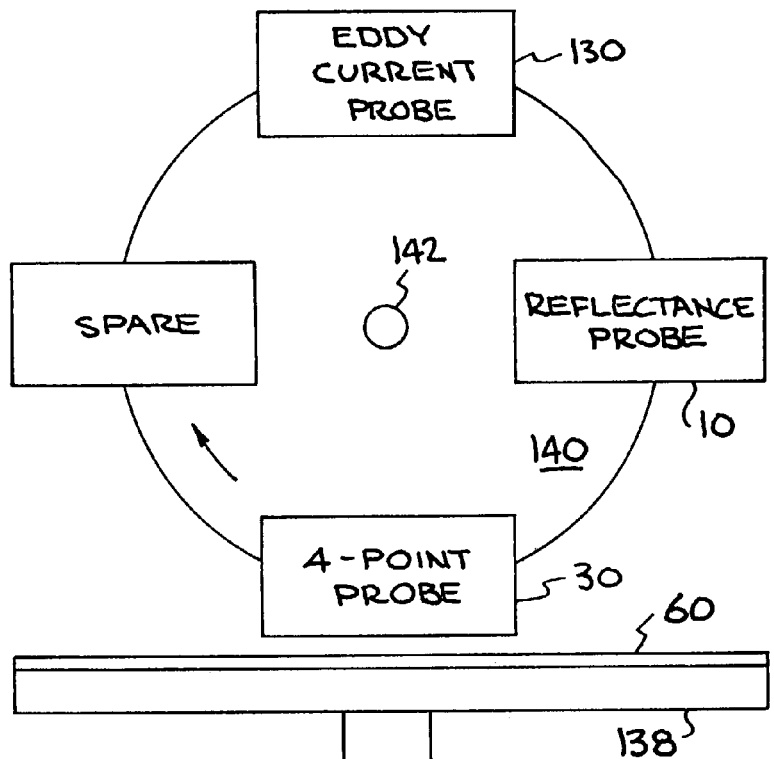
FIG. 7 is a side view of a carousal mechanism used to move various probes for measuring, over the same or nearly the same area of the thin film being tested, the sheet resistance and reflectance of the thin film.
Figure 8:
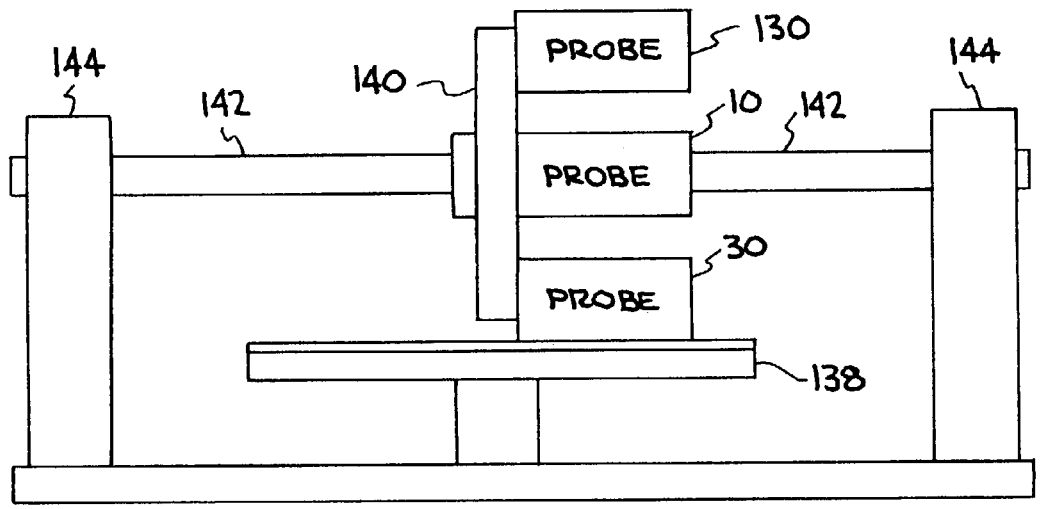
FIG. 8 is a cross-axis view of the structure of FIG. 7.

Turning now to FIGS. 7 and 8, yet another embodiment of the invention is shown wherein reflectance and sheet resistance measurements are made sequentially on the same portion of a thin film 60 mounted on a platform 138.

Above thin film 60 and platform 138 is a wheel or carousel 140 which is secured to a rotatable shaft 142. Supports 144 are located on the ends of shaft 142. On wheel 140 are mounted the various probes for respective measurement of reflectance and sheet resistance in accordance with the invention. In the illustrated embodiment of the invention shown in FIGS. 7–8, a reflectance probe 10, a 4 point sheet resistance probe 30, and an eddy current sheet resistance probe 130 are all mounted 90 degrees apart on wheel 140, with provision for a fourth probe to be mounted on the fourth 90° station on rotating wheel 140.

The process of the invention can, in any of the illustrated embodiments, therefore, provide an integrated delivery of data concerning the sheet resistance and reflectivity of a thin film in a more accurate and timely fashion while conserving processing time and saving on equipment costs as well as equipment process time. Furthermore, by measuring both reflectance and sheet resistance of a particular surface area, a more accurate determination may be made of the thickness of the thin film in the portion measured.

Having thus described the invention what is claimed is:

1. A process for determining the thickness of a thin film by measuring both the reflectance and sheet resistance of said thin film in the same measurement apparatus comprises:
   a) mounting a thin film in said chamber;
   b) mounting in said same measurement apparatus an apparatus capable of measuring the sheet resistance of said thin film;
   c) mounting a reflectance apparatus in said same measurement apparatus adjacent said sheet resistance measurement apparatus;
   d) directing a beam of radiation from a radiation source of said reflectance apparatus onto a portion of the surface of said thin film in said measurement apparatus;
   e) sensing the radiation reflected from said surface of said thin film to measure the reflectance of the surface of said thin film;
   f) determining the resistivity of said thin film from said measured reflectance of said thin film
   g) contacting a portion of said surface of said thin film adjacent said portion of said thin film contacted by said radiation beam, to measure the sheet resistance of said thin film in said measurement apparatus; and
   h) determining the thickness of said thin film from said resistivity and said measured sheet resistance.

2. The process of claim 1 wherein said step of directing a beam of radiation from said radiation source onto a portion of the surface of said thin film further comprises using fiber optics to transmit said radiation beam onto said portion of said surface of said thin film.

3. The process of claim 1 wherein said step of directing a beam of radiation from said radiation source onto a portion of the surface of said thin film further comprises passing said radiation though a lens assembly in said reflectance measurement apparatus to focus said radiation beam onto said portion of said surface of said thin film.

4. The process of claim 1 wherein said step of directing a beam of radiation from said radiation source onto a portion of the surface of said thin film further comprises mounting said reflectance measurement apparatus adjacent said sheet resistance measurement apparatus.

5. The process of claim 1 wherein said sheet resistance measurement apparatus comprises a 4 point probe measurement apparatus.

6. The process of claim 5 wherein said step of directing a beam of radiation from said radiation source onto a portion of the surface of said thin film further comprises mounting said reflectance measurement apparatus adjacent said 4 point probe sheet resistance measurement apparatus.

7. The process of claim 5 wherein said step of directing a beam of radiation from said radiation source onto a portion of the surface of said thin film further comprises mounting said four pins of said 4 point probe sheet resistance measurement apparatus around said reflectance measurement apparatus.

8. The process of claim 5 wherein said step of directing a beam of radiation from said radiation source onto a portion of the surface of said thin film further comprises mounting said four pins of said 4 point probe sheet resistance measurement apparatus adjacent one side of said reflectance measurement apparatus.

9. The process of claim 1 wherein said thin film comprises a film selected from the group consisting of a metal film, a doped semiconductor film, and an insulating film.

10. The process of claim 9 wherein said thin film is a metal film.

11. The process of claim 9 wherein said thin film is a doped semiconductor film.

12. A process for determining the thickness of a thin film of doped silicon by measuring both the reflectance and sheet resistance of said thin film of doped silicon in the same measurement apparatus comprises:
   a) mounting a thin film of doped silicon in said measurement apparatus;
   b) mounting in said same measurement apparatus an apparatus capable of measuring the sheet resistance of said thin film of doped silicon;
   c) mounting a reflectance apparatus in said same measurement apparatus adjacent said sheet resistance measurement apparatus;
   d) directing a beam of radiation from a radiation source of said reflectance apparatus onto a portion of the surface of said thin film of doped silicon in said measurement apparatus;
   e) sensing the radiation reflected from said surface of said thin film of doped silicon to measure the reflectance of the surface of said thin film of doped silicon;
   f) determining the resistivity of said thin film of doped silicon from said measured reflectance of said thin film of doped silicon;
   g) contacting a portion of said surface of said thin film of doped silicon adjacent said portion of said thin film of doped silicon contacted by said radiation beam, to measure the sheet resistance of said thin film of doped silicon in said measurement apparatus; and
   h) determining the thickness of said thin film of doped silicon from said resistivity and said measured sheet resistance.

13. The process of claim 12 wherein said step of directing a beam of radiation from said radiation source of said reflectance apparatus onto a portion of said surface of said thin film further comprises transmitting said beam of radiation onto said portion of said surface of said thin film using fiber optics.

14. The process of claim 12 wherein said step of directing a beam of radiation from said radiation source of said reflectance apparatus onto a portion of said surface of said thin film further comprises passing said radiation though a lens assembly in said reflectance apparatus to focus said radiation beam onto said portion of said surface of said thin film.

15. The process of claim 12 wherein said step of measuring said reflectance of said thin film is carried out simultaneous with said step of measuring the sheet resistance of said thin film.

16. The process of claim 15 wherein said step of measuring said reflectance of said thin film and said step of measuring the sheet resistance of said thin film are carried out simultaneously on the same said portion of said surface of said thin film.

17. The process of claim 15 wherein said step of measuring said reflectance of said thin film and said step of measuring the sheet resistance of said thin film are carried out simultaneously on adjacent portions of said surface of said thin film.

18. The process of claim 12 wherein said step of measuring said reflectance of said thin film and said step of measuring the sheet resistance of said thin film are carried out sequentially.

19. The process of claim 18 wherein said step of measuring said reflectance of said thin film and said step of measuring the sheet resistance of said thin film are carried out sequentially by first measuring said reflectance of said thin film and then measuring the sheet resistance of said thin film.

20. The process of claim 18 wherein said step of measuring said reflectance of said thin film and said step of measuring the sheet resistance of said thin film are carried out sequentially on the same said portion of said surface of said thin film.

21. The process of claim 18 wherein said step of measuring said reflectance of said thin film and said step of measuring the sheet resistance of said thin film are carried out sequentially on adjacent portions of said surface of said thin film.

22. The process of claim 18 wherein said thin film comprises a film selected from the group consisting of a metal film, a doped semiconductor film, and an insulating film.

23. The process of claim 12 which also includes determining the thickness of the thin film by the further steps of:
   a) determining the resistivity of the thin film from said measured reflectance of said thin film; and
   b) dividing said resistivity by said measured sheet resistance to determine the thickness of said thin film.

24. A process for determining the thickness of a thin film by measuring both the reflectance and sheet resistance of said thin film in the same or adjacent positions on said same thin film comprises:
   a) mounting in a measurement apparatus a 4 point probe apparatus capable of measuring the sheet resistance of said thin film;
   b) mounting a reflectance apparatus in the same measurement apparatus adjacent said 4 point sheet resistance apparatus;
   c) mounting a thin film in said measurement apparatus;
   d) directing a beam of radiation from a radiation source of said reflectance apparatus onto a portion of the surface of said thin film in said measurement apparatus;
   e) sensing the radiation reflected from said surface of said thin film to measure the reflectance of the surface of said thin film;
   f) determining the resistivity of said thin film from said measured reflectance of said thin film;
   g) contacting, with said 4 point probe, a portion of said surface of said thin film surrounding said portion of said thin film contacted by said radiation beam, to measure the sheet resistance of said thin film in said measurement apparatus and
   h) dividing said resistivity by said measured sheet resistance to determine the thickness of said thin film.

* * * * *